United States Patent [19]
Kahn et al.

[11] Patent Number: 5,105,807
[45] Date of Patent: Apr. 21, 1992

[54] DEVICE AND METHODS FOR SECURING NASAL TUBING

[75] Inventors: Mark J. Kahn, Gainesville; Michael Wood, Archer, both of Fla.

[73] Assignee: Alternative Medical Products, Inc., Gainesville, Fla.

[21] Appl. No.: 661,279

[22] Filed: Feb. 26, 1991

[51] Int. Cl.$^5$ ................ A61M 15/08; A62B 7/00
[52] U.S. Cl. .................. 128/207.18; 128/DIG. 26; 128/911; 128/912; 128/200.26; 128/204.12
[58] Field of Search ............. 128/911, 912, DIG. 26, 128/206.18, 207.13, 207.18, 200.24, 200.26, 204.12; 606/198, 199

[56] References Cited

U.S. PATENT DOCUMENTS

| | | | |
|---|---|---|---|
| 3,915,173 | 10/1975 | Brekke | 128/207.18 |
| 4,648,398 | 3/1987 | Agdanowski et al. | 128/207.18 |
| 4,736,741 | 4/1988 | Payton et al. | 128/207.18 |
| 4,821,715 | 4/1989 | Downing | 128/207.18 |

Primary Examiner—Edgar S. Burr
Assistant Examiner—Lisa E. Malvaso
Attorney, Agent, or Firm—Saliwanchik & Saliwanchik

[57] ABSTRACT

Disclosed are a novel device and novel methods for securing nasal tubing in medical patients. The invention provides, with minimal trauma, discomfort, and distraction to the patient, a means of securing in place nasal tubing inserted through the nasal passage. In addition, the disclosed invention provides a device which can be replaced without removal of a nasal tube already in place.

20 Claims, 5 Drawing Sheets

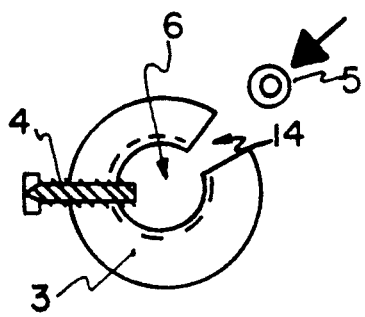
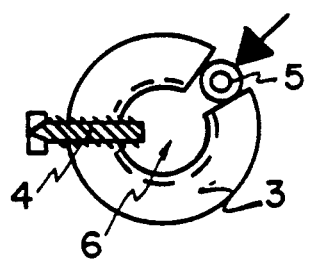
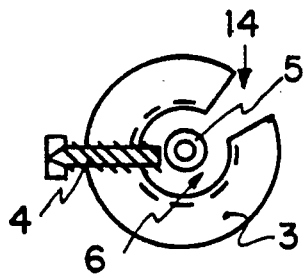
Fig. 3a      Fig. 3b      Fig. 3c
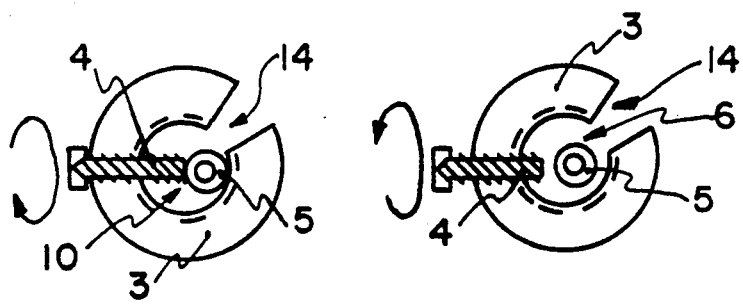
Fig. 3d      Fig. 3e

DEVICE AND METHODS FOR SECURING NASAL TUBING

BACKGROUND OF THE INVENTION

Tubing inserted through the nasal passage of medical patients is used to introduce oxygen, or air, or other fluid treatments into the nasopharyngeal area or directly into the airway. In addition, tubing inserted through the nasal passage of patients is used to provide a means of introducing fluids into, or extracting fluids from, the gastrointestinal tract.

Once the tubing is inserted through the nasal passage and appropriately positioned to achieve the desired treatment, a means of securing the tubing is necessary to maintain that placement. Treatments administered to the patient by the nasal tube method can require that the tubing remain in place for up to several hours or days or longer. Therefore, it is especially important to provide a means of securing nasal tubing in a particular position for extended periods while providing maximum comfort for the patient. Furthermore, to maintain appropriate health care standards and to minimize trauma and irritation to the patient, the nasal tube securing system should preferably provide for a means of replacing the securing system while the nasal tubing remains in place. Thus, two distinct means of securing the nasal tubing are required. First, the tubing must be attached to, and easily detachable from, a positioning device which holds the tubing in its proper position to effectively deliver fluids to, or remove fluids from, the patient. Second, the positioning device must be comfortably secured to, and easily detachable from, the patient. Convenience and time efficiency regarding attachment are important considerations.

The most common method currently used to attach nasal tubing to patients involves taping the tube to the patient's face. Generally, surgical tape or similarly employed adhesive pads are used to anchor the nasal tubing to the skin of the patient. The primary drawback of this method is that the patient's face can become irritated and sore as a result of repeated application and removal of the tape. Obviously, this method is particularly unacceptable for burn patients or patients with other facial wounds. If tape with reduced adhesion is used, skin trauma can be lessened, but the nasal tube may not be held securely.

Various alternatives to the conventional use of tape have been suggested but certain limitations of these alternatives have prevented them from being widely accepted. For example, currently available alternative means for securing nasal tubing to patients include a device which has two sponge-like tips for placement into both nostrils attached at the terminal ends of the nasal tubing (Agdanowski et al., U.S. Pat. No. 4,648,398); flexible finger-like projections which extend outward and abut the inner surface of the nostril (Payton et al., U.S. Pat. No. 4,736,741); a hook attached to an intranasally placed device which said hook is of a material with appropriate elasticity to conform to the contour of the nostril and effectively clamp in place the attached intranasally placed device (Downing et al., U.S. Pat. No. 4,821,715); and, a tube having a balloon-type inflatable outer wall which secures behind constrictions in the airway or gastrointestinal tract (Brekke, U.S. Pat. No. 3,915,173).

The currently available means of securing nasal tubes pose a variety of problems which include the inability to change or replace the attachment device without also removing the nasal tubing, physical discomfort and irritation to the patient, as well as unpleasant aesthetics. For example, the current means available which employ the use of a securing device having a lumen through which the nasal tube passes, requires that the nasal tube be removed while replacing the securing device. The removal of the nasal tube while replacing the securing device results in interruption of the treatment. Proper hygienic procedures and health care standards require the periodic replacement of the attachment devices several times per day. Moreover, the means used to secure the nasal tubing to the securing device occludes the lumen surrounding the nasal tube and prohibits adequate draining of normal nasal discharge. Lumen occlusion also prevents maintaining patency of the airway required for normal respiration. In addition, the current means employing adherents applied to the face cause irritation and trauma to the skin and hair, especially upon repeated removal and replacement. Furthermore, devices applied to the face or within the visibility of the patient increase patient distraction and emotional discomfort.

Another source of irritation and discomfort to the patient derives from the nasal tubing itself. Physical contact between the nasal tubing and the mucous membranes lining the nasal passage can cause irritation, trauma, and scarring. An often overlooked factor which can increase tissue damage results when gastric fluids migrate via capillary action from the stomach to the nasal area. The gastric fluids are of relatively high acidity and can cause chemical irritation to the membranes. These gastric fluids actually permeate through the nasal tubing and irritate the surrounding nasal tissue while the tube remains in place. A securing means which prevents contact and provides an actual physical barrier between the nasal tubing and the inner nostril can, therefore, reduce the resulting irritation.

Hence, it is an objective of the present invention to provide a novel and improved means of securing nasal tubing which alleviates or mitigates one or more of the above-mentioned problems.

BRIEF SUMMARY OF THE INVENTION

The "DNAS" unit (Disposable Nasal Anchoring System) is a device designed to allow nasal tubing to be conveniently secured to medical patients without the use of adhesive tape as is the present common practice. The device has been designed with a variety of different functional priorities, mostly centered around the comfort of the patient and convenience of use for the person securing the device to the patient.

The DNAS unit comprises a compressible sleeve, preferably of sponge-like material, which fits over and surrounds a hollow support tube. The hollow tube and compressible sleeve can be inserted into a patient's nostril. To facilitate this insertion, the compressible sleeve can be compressed. Once inside the nostril, the sleeve gently expands to hold the device firmly in place. The support tube provides a means of preventing total collapse of the sleeve during compression of said sleeve. Thus, this hollow support tube comprises a lumen through which a nasal tube can be passed into the nasal passage. A hub, which can be an integral part of the support tube, facilitates manipulation and placement of the device. The hub additionally provides a convenient and functional site wherein can be attached a nasal tube locking device. This device holds the nasal tubing securely in place within the hollow support tube.

Advantageously, the locking device of the subject invention holds nasal tubing securely within the hollow support tube while leaving space between the nasal tubing and the inside wall of the support tube so that normal nasal drainage can occur through the lumen of the support tube and peripheral to the nasal tube.

The primary intent of the DNAS unit, shown in FIG. 1, is to improve the quality of health care and the comfort of the patient, while simultaneously decreasing the time and effort required of the medical staff to implement the basic procedure of securing nasal tubing in patients.

BRIEF DESCRIPTION OF THE DRAWINGS

FIG. 3 shows cross-sectional detail of the split sheath DNAS unit and configuration for removing/replacing the DNAS unit from around the nasal tube 5. FIG. 3(a) shows the nasal tubing outside the DNAS unit, FIG. 3(b) shows placement through the split sheath, and FIG. 3(c) shows the nasal tubing within the lumen 6 of the hub 3. FIG. 3(d) shows the set screw locking means 4 securing the nasal tubing 5 within the lumen 6 of the hub 3, and FIG. 3(e) shows release of the locking means 4 by counterclockwise rotation.

DETAILED DESCRIPTION OF THE INVENTION

Figure 1A:
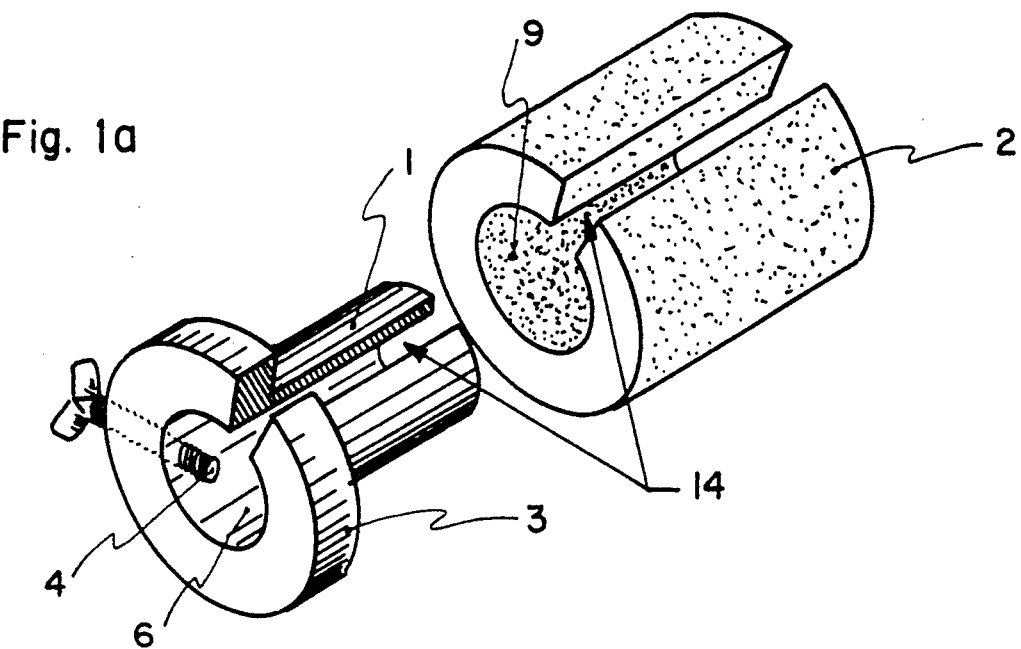
FIG. 1 shows a split sheath DNAS device with (a) the compressible sleeve 2 separated from the support tube 1 and hub 3, and (b) the compressible sleeve 2 attached to the support tube 1 and hub 3.
FIG. 1(b) also shows the configuration with respect to the nasal tubing 5 secured by set screw locking means 4.

The DNAS device as shown in FIG. 1 provides a novel means for securing nasal tubing in medical patients. The invention described herein comprises a support tube 1, of which the inner wall defines a lumen 6 through which a nasal tube can pass into the nasal passage of a patient. The device further comprises a compressible sleeve 2, an integral or immovably attached hub 3, and a nasal tube locking device 4. The hub 3 is positioned at one end of the support tube 1 as an integral or immovable part of the support tube and is designed to facilitate handling and placement of the DNAS device. Additionally, the hub 3 provides a support base for a nasal tube locking device 4.

Figure 1B:
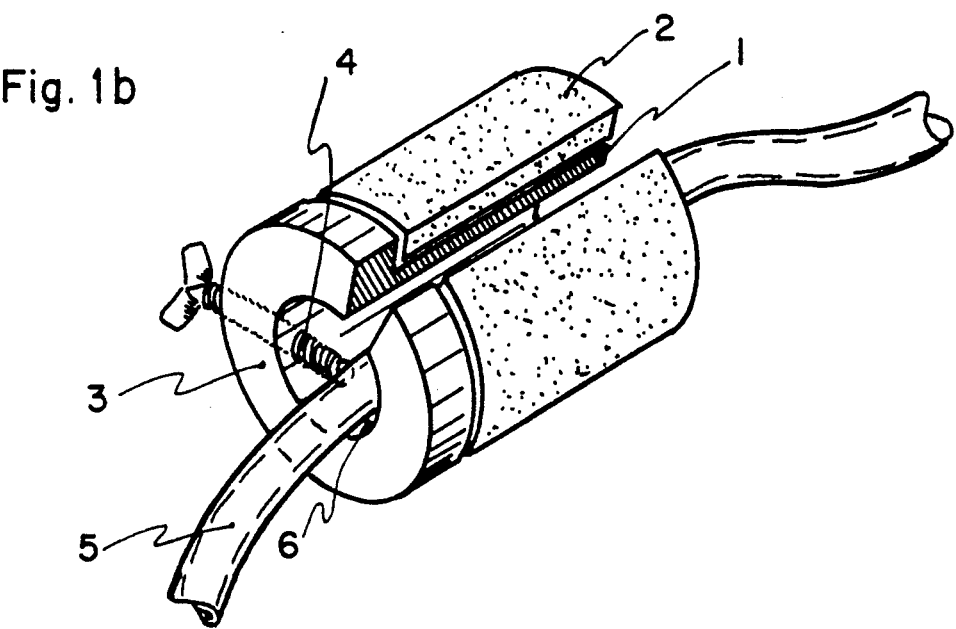

The locking device 4 of the subject invention holds the nasal tubing 5 securely within the lumen 6 of the hollow support tube 1 as shown in FIG. 1(b). The locking device 4 prevents the nasal tubing 5 from slipping out of the nostril or otherwise sliding back and forth through the nasal tubing anchoring device 4. Consequently, patients are able to move their heads or make other normal motions without concern about loosening or causing slippage of the nasal tube. Also, the health professional may position the tubing with confidence, knowing that the tubing will not easily be moved by normal movements of the patient. Because the outside diameter of the nasal tubing is smaller than the inside diameter of the hollow support tube, the nasal tube would be free to slide back and forth within the hollow support tube if it were not for the locking device which holds the nasal tube in place.

It is highly advantageous to have the nasal tubing 5 be of a smaller diameter than the inside diameter of the support tube 1 because this leaves a space in the lumen 6 through which ordinary nasal drainage can occur. Without this space between the nasal tubing and the inside wall of the support tube, drainage and air movement could not occur. Without drainage, the patient is more susceptible to discomfort and infection. Without air movement, it is more difficult for the patient to breathe. Also, discomfort may result, and the device could be dislodged by pressure resulting from a sneeze or attempts to breathe through the nose.

Another important advantage of the described invention arises due to protection of the nasal tissue from acidic gastric fluids. A nasal tube contacting gastric fluids will absorb and/or adsorb these fluids into the nasal tube material itself. Capillary action causes the gastric fluids to migrate into the nasal area. Diffusion of the gastric fluids through the tubing allows relatively low pH fluids to be present at the outside surface of the nasal tubing. With the use of conventional means for securing nasal tubing, the outside of the nasal tubing and, hence, the acidic gastric fluids, can come into direct contact with the sensitive nasal tissues. The present invention forms a physical barrier around the nasal tubing, preventing the acid-permeated tubing from contacting the nasal membrane. The nasal lining is, thus, protected by a double barrier. First, the lumen inside the support tube separates the nasal tube from the DNAS device. Second, the interior support tube and compressible sleeve of the DNAS unit further prevent contact between the nasal tube and the nasal tissue by providing an additional barrier.

Figure 2A:
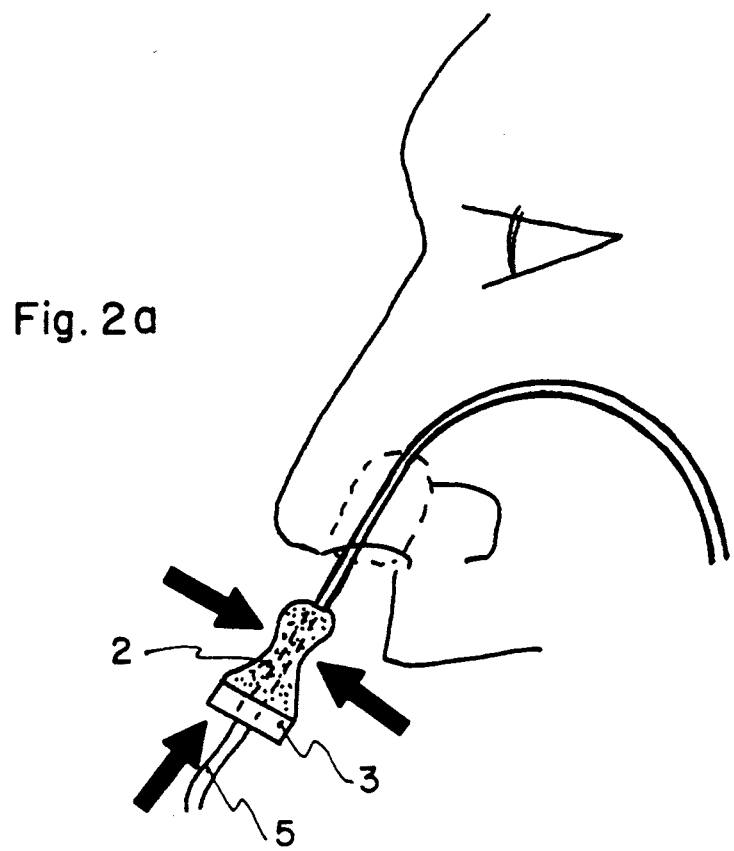
FIG. 2 shows the DNAS device with (a) compressible sleeve 2 compressed prior to insertion into the nostril of a patient, and (b) the DNAS unit inserted into the nostril with sleeve 2 expanded to its original shape which secures the unit in place within the nostril.
Figure 2B:
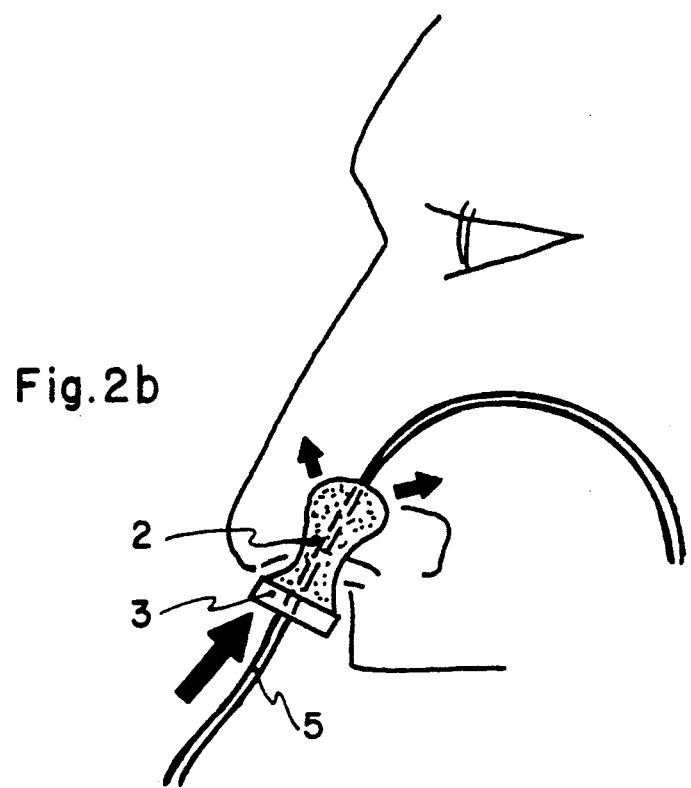
Figure 4A:
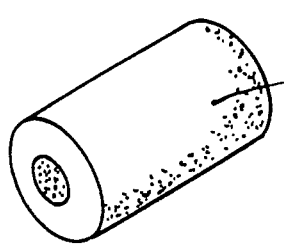
FIG. 4 shows a sample of the various basic shapes that can be used as a compressible sleeve 2 for the DNAS device. The shapes shown in FIGS. 4(a)-(d) refer to the radial cross-sectional shape and include: (a) circular, (b) polygonal, (c) oval, and (d) rectangular. Modifications of the sleeve which can be adapted according to need or desirability include: (e) cone-shape, (f) cylindrical shape with internal channels 7, and (g) irregular shape which forms external channels 8.
Figure 4B:
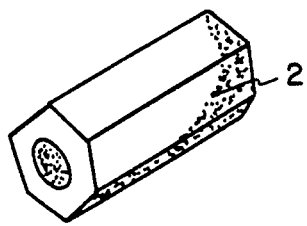
Figure 4C:
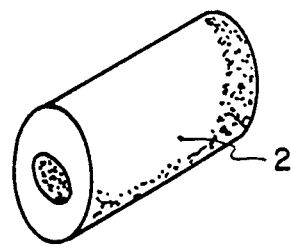
Figure 4D:
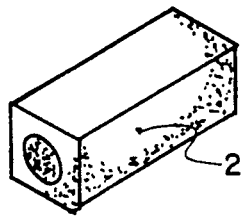
Figure 4E:
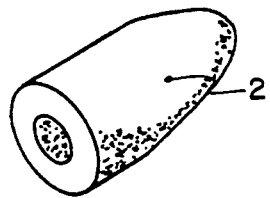
Figure 4F:
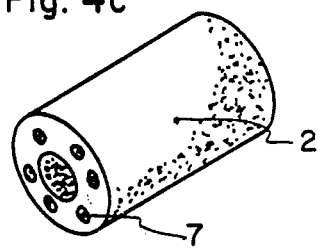
Figure 4G:
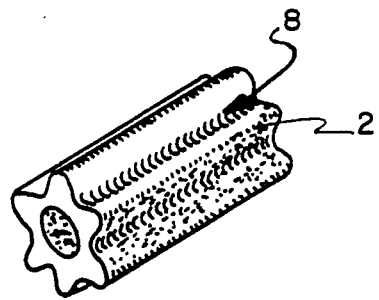

Abutting the hub 3 and encompassing the outer wall of the support tube 1 is a compressible sleeve 2 which comfortably secures the device inside the nostril of a patient (see FIG. 2). In one preferred embodiment, the compressible sleeve can be permanently bonded to the support tube.

As shown in FIG. 3, to further secure nasal tube placement in a patient, a locking device 4, which comprises a set screw clamp, can be attached to the hub. To preserve the passageway through the lumen 6 between the nasal tube 5 and the support tube 1, the locking device 4, which secures the nasal tube 5 in place, should not block this passageway. As shown in FIG. 3(d), one preferred locking device 4 is a set screw which passes through the hub 3 and contacts the nasal tubing 5 at a discrete point such that the air passageway through the lumen 6 is not eliminated.

The nasal tube securing device of the subject invention (also known as DNAS) can be used in animal health care applications as well as in human health care. The device can be readily manufactured in a variety of dimensions to be used with animals of all sizes. The device is used in the same way, and with the same advantages, when used with animals. Thus, as used herein, the term "patients" is understood to refer to both humans and animals.

The following are examples of each of the individual components of the novel device. These examples illustrate materials, methods, and procedures, including the best mode, for practicing the invention. These descriptions should not be construed as limiting.

EXAMPLE 1—COMPRESSIBLE SLEEVE

The DNAS device of the subject invention utilizes a compressible sleeve designed to facilitate insertion into the nostril. The sleeve comfortably maintains the position of the device in the nostril of the patient, eliminating the physical trauma to the skin and emotional stress caused by the commonly used large strips of adhesive tape placed across the face of the patient. The sleeve itself can be made of a soft, sponge-like foam or rubber material which, when compressed, has the "memory" to return to its original shape and size. The sleeve material can be such that the sleeve is impermeable and therefore less susceptible to damage caused by nasal discharge and other moisture. Alternatively, the sleeve material can be coated with a patient-compatible material which renders the sleeve impermeable.

The shape of the sleeve may vary based on usage needs. In one preferred embodiment, the sleeve can be a hollow cylindrical shape. Alternatively, as shown in FIG. 4, many adaptations of the shape can be used to fulfill the purpose of the compressible sleeve. The various shaped sleeves can also contain channels 7 which run the axial length of the sleeve and provide an additional outlet for normal nasal discharge and airflow. These channels can additionally be formed between the outside of the sleeve 8 and the inside of the nostril by irregularly shaped sleeves. The channel surfaces should also be impermeable. The size and length also may vary considerably. Shorter lengths and smaller diameter sleeves can be used for younger patients with smaller nasal cavities.

The sleeve is designed to be compressed and, while still in a compressed state, inserted into the nostril. After insertion, the sleeve gently expands to conform to the nasal cavity of the patient. This method, shown in FIG. 2, puts only slight pressure in the nostril, and is considerably more comfortable than the old method of anchoring with adhesive tape. The pressure of the sleeve of the device in the nostril is sufficient to hold the nasal gastric tubing in place despite normal patient movement.

To further prevent slippage during placement or removal of the DNAS unit, the compressible sleeve can be permanently attached to the support tube. The attachment of the compressible sleeve to the inner support tube can be achieved by use of an adhesive or the sleeve and inner support tube can be molded in the manufacturing process as a single unit.

Another embodiment of the compressible sleeve comprises the use of inflatable, balloon-like material to provide a securing means within the nostril of the patient. In this embodiment, the sleeve which encircles the support tube can be inflated with air or liquid which causes the sleeve to expand inside the nostril and apply gentle pressure against the inner wall which is adequate to secure the DNAS unit in place. Preferably, the inflatable sleeve would be affixed with a standard syringe-compatible valve which would facilitate inflation and deflation.

EXAMPLE 2—INTERIOR SUPPORT TUBE

As illustrated in FIG. 1, at the interior of the compressible sleeve 2 there is a support tube 1 made of plastic or other suitable rigid material such as ceramic rubber or metal. Preferably, this material is more rigid than the sleeve. The support tube is designed to guide nasal tubing 5 through the sleeve 2, allow for the passage of air, and allow for the securing of nasal tubing with the locking device 4 described below. This inner support tube 1 can have various diameter sizes, ranging from about 0.010 to about 0.250 inch inner diameter to allow for different sizes of nasal tubing. The inside diameter of the rigid support tube should be sufficient to allow room between the nasal tubing and the inside wall of the support tube. This room between the outer and inner walls of the two tubes allows for normal nasal drainage and air movement. This inner support tube 1 also provides support to the compressible sleeve 2, maintaining a permanent passageway and preventing the total collapse of the sleeve lumen 9 when the sleeve is compressed.

EXAMPLE 3—SUPPORT TUBE "HUB"

In one embodiment of the subject invention, as shown in FIG. 1, the interior support tube 1 described above can incorporate a "hub" 3 as an integral or immovably attached part of the support tube 1. The hub 3 can be located at the distal end of the support tube 1. Thus, the hub 3 is designed to be outside the patient's nostril. The hub 3, also preferably constructed of plastic or other rigid material, such as ceramic, rubber, or metal, allows a locking device 4, as described below, to have sufficient strength, threading surface, and position on the support tube 1. Thus, the hub 3 can function as a foundation for the locking means 4. The hub also allows for easier positioning of the compressible sleeve 2 in the proper place in the nostril, by providing a more rigid surface for handling.

EXAMPLE 4—LOCKING MEANS

The DNAS is designed to incorporate a locking means which, through use of a set-screw clamp or other appropriate securing means, secures nasal tubing to the support tube and/or to the hub. This locking feature is designed to prevent the nasal tubing from being displaced by patient movement, to prevent discomfort to the patient caused by traditional adhesive tape methods of anchoring, and to reduce the need for a health professional having to reposition or replace nasal tubing. As shown in FIG. 3(d), the locking means 4 functions so as to leave a passageway 10 between the nasal tubing 5 and the support tube and hub 3 which permits drainage and respiration. Allowing drainage prevents a build-up of fluids behind the device, thus preventing fluids from draining back into the patient's sinuses or throat. This greatly reduces the potential for sinus infections and pneumonia and reduces minor discomfort and other problems which could arise if drainage were not freely permitted.

The continuously open passageway provided according to the subject invention also gives the patient the ability to maintain respiration through the nostril, which relieves pressure behind an inserted device. Without the open passageway, this pressure can cause the patient to dislodge or discharge the device by coughing, sneezing, or any attempt at exhalation through the nose.

A variety of locking means can function to secure the nasal tubing within the lumen of the support tube. One preferred locking means, shown in FIG. 3, is a set-screw 4 which is tapped through threads in the support tube or hub 3, penetrating into the lumen 6 of the support tube or hub and then securing the nasal tubing 5 in place by being screwed down onto the nasal tubing. The set screw version of the locking means can be seen in FIGS. 1, 2, and 3. The setscrew can comprise a bent "elbowed" end to facilitate turning by hand, and threads sized so as to allow securement in only ¼ to ½ rotations of the screw.

Figures 5A, 5B, 5C:
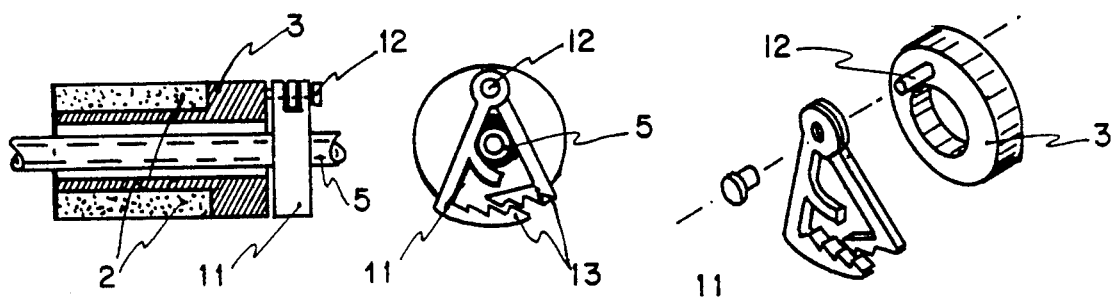
FIG. 5 shows (a) side view, (b) front view, and (c) exploded perspective view of a DNAS device with "locking hub" 11 attached to support tube 1 via support post 12.

Other locking means available to accomplish securing of the tubing while maintaining patency of the passageway are the clamp or the rotating constriction lock. The clamp 11, which is shown in FIG. 5, and the rotating lock both can be fitted on posts 12 in front of the hub 3 at the end opposite the compressible sleeve 2. The clamp (or vise) version acts in such a way as to clamp or pinch the nasal tube 5 without significantly constricting the diameter of the nasal tube, securing it in place, as shown in FIG. 5(b). The rotating version rotates to decrease the inner diameter of the lock until it has secured the tubing without restricting the diameter of the nasal tube. The locking systems can be produced from a variety of materials including metal and plastic. The material must be of sufficient rigidity and strength to effectuate securing the nasal tubing without breaking or buckling of the locking system. The locking means may also comprise interlocking teeth 13, grooves, notches, or serrations.

EXAMPLE 5—THE SPLIT SHEATH DNAS

FIG. 1 shows a "split sheath" which is descriptive of an arrangement whereby the interior support tube has a slot 14 running the axial length of the support tube 1, including the hub 3. The width of the slot 14 is approximately the same size as the outer diameter of standard nasal tubing 5 (see also FIG. 3). Different slot widths could be used for different applications. In this embodiment, the compressible sleeve 2 also has a slot 14 along its length. The slot 14 in the support tube 1, hub 3, and compressible sleeve 2 allows for removal of the DNAS unit without the removal of the nasal tubing 5 from the patient. This simplifies the replacement of the DNAS unit, as must be done routinely for health and comfort reasons. Without this split sheath, the nasal tube must be completely removed from the patient in order to replace the DNAS unit. The replacement of a DNAS device while the nasal tube remains in place is significantly less complicated than replacing adhesive tape while maintaining the nasal tube in place.

With current procedures, adhesive tape must be changed frequently to prevent facial skin trauma. This is an awkward and time-consuming process for the person removing and replacing the adhesive tape. Replacing the DNAS unit simply requires its removal from the nasal tubing by aligning the split sheath in a manner which allows the nasal tube to pass through the slot. Likewise, replacement with a new DNAS unit is accomplished by inserting the nasal tubing through the slot of the split sheath. This new method causes no discomfort to the patient and is quick and easy for a person employing the novel DNAS unit as a nasal tube securing device.

Other embodiments within the scope of the subject invention that allow replacement of the DNAS unit without removal of the nasal tubing include (a) a "hinged" unit or (b) a "perforated" unit. The hinged unit comprises the above-described sleeve, support tube, and hub manufacture in two opposing, symmetric halves which fasten together along the axial length of the unit. One of the two junctures can comprise a hinge so that the two halves open and allow the DNAS unit to be removed from around the nasal tube which remains in place.

The perforated unit comprises two opposing, symmetric halves as described in the hinged unit. However, one or both junctures are attached by a perforated seam which can be separated to allow removal of the DNAS unit from around the nasal tubing, while the nasal tubing remains in place.

EXAMPLE 6—KITS

For convenience, components for the nasal tube securing device can be assembled in kits. A kit to facilitate the securing of a nasal tube in a patient can include either or both of the following:

(a) a device for securing nasal tubing in patients, said device comprising a hollow support tube comprising a lumen through which said nasal tubing can pass, said device further comprising a compressible sleeve which surrounds said support tube and a locking means which is capable of holding said nasal tubing in a fixed position within said support tube; and (b) nasal tubing.

If the compressible sleeve comprises an inflatable balloon-type apparatus comprising a valve, an additional element of the kit can be a syringe which facilitates inflation and deflation of the device.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A device for securing nasal tubing in patients, said device comprising a hollow support tube comprising a lumen through which said nasal tubing can pass, said device further comprising a compressible sleeve which surrounds said support tube and a locking means which is capable of holding said nasal tubing in a fixed position within said support tube.

2. The device, according to claim 1, which further comprises a hub located at the distal end of said support tube wherein said hub is integrally joined to said support tube or is immovably attached to said support tube, wherein said hub can function as a foundation for said locking means.

3. The device, according to claim 2, wherein said support tube and said hub are made of a rigid material selected from the group consisting of plastic, ceramic, rubber, and metal.

4. The device, according to claim 1, wherein said compressible sleeve comprises a resilient foam or rubber which, following compression, returns to its original shape and size at a rate which enables said sleeve to secure said device in the nostril of a patient by the pressure of said sleeve against said nostril.

5. The device, according to claim 1, wherein said locking means comprises a threaded screw which protrudes through said support tube or said hub into said lumen of said device at an angle and a distance sufficient to secure a nasal tube passed through said lumen.

6. The device, according to claim 1, wherein said locking means comprises a clamp.

7. The device, according to claim 6, wherein said clamp comprises interlocking teeth.

8. The device, according to claim 1, wherein said locking means comprises a rotating constriction lock.

9. The device, according to claim 1, wherein said support tube and said compressible sleeve comprise a split sheath comprising a slot which runs the axial length of said device to facilitate removal of said device while maintaining the position of said nasal tubing.

10. The device, according to claim 2, wherein said support tube, said compressible sleeve, and said hub comprise a split sheath comprising a slot which runs the axial length of said device to facilitate removal of said device while maintaining the position of said nasal tubing.

11. The device, according to claim 1, wherein said locking means permits passage of a nasal tube through said support tube while drainage, respiration, and pressure release are facilitated by maintaining, unoccluded, said lumen of said support tube.

12. A method for securing nasal tubing in a patient, said method comprising:
 (1) providing a device, said device comprising a hollow support tube comprising a lumen through which said nasal tubing can pass, said device further comprising a compressible sleeve which surrounds said support tube and a locking means which is capable of holding said nasal tubing in a fixed position within said support tube;
 (2) compressing said compressible sleeve;
 (3) inserting said device into the nostril of said patient; and
 (4) locking said nasal tubing in a fixed position within said locking means.

13. The method, according to claim 12, wherein said device further comprises a hub located at the distal end of said support tube wherein said hub is integrally joined to said support tube or is immovably attached to said support tube, wherein said hub can function as a foundation for said locking means.

14. The method, according to claim 13, wherein said support tube and said hub are made of a rigid material selected from the group consisting of plastic, ceramic, rubber, and metal.

15. The method, according to claim 12, wherein said compressible sleeve comprises a resilient foam or rubber which, following compression, returns to its original shape and size at a rate which enables said sleeve to secure said device in said patient's nostril by the pressure of said sleeve against said nostril.

16. The method, according to claim 12, wherein said locking means comprises a threaded screw which protrudes through said support tube or said hub into said lumen of said device at an angle and a distance sufficient to secure a nasal tube passed through said lumen.

17. A method, according to claim 12, wherein said support tube and said compressible sleeve comprise a split sheath comprising a slot which runs the axial length of said device.

18. The method, according to claim 13, wherein said support tube, said compressible sleeve, and said hub comprise a split sheath comprising a slot which runs the axial length of said device.

19. The method, according to claim 12, wherein said locking means permits passage of a nasal tube through said support tube while maintaining, unoccluded, said lumen of said support tube.

20. A kit providing means for securing nasal tubing in a patient, said kit comprising:
 (a) a device for securing nasal tubing in patients, said device comprising a hollow support tube comprising a lumen through which said nasal tubing can pass, said device further comprising a compressible sleeve which surrounds said support tube and a locking means which is capable of holding said nasal tubing in a fixed position within said support tube; and
 (b) nasal tubing.

* * * * *

UNITED STATES PATENT AND TRADEMARK OFFICE
CERTIFICATE OF CORRECTION

PATENT NO. : 5,105,807

DATED : April 21, 1992

INVENTOR(S) : Mark J. Kahn, Michael Wood

It is certified that error appears in the above-identified patent and that said Letters Patent is hereby corrected as shown below:

Column 6: line 8, "ceramic rubber or metal" should read -- ceramic, rubber, or metal --.

Signed and Sealed this

Third Day of August, 1993

Attest:

MICHAEL K. KIRK

Attesting Officer     Acting Commissioner of Patents and Trademarks